United States Patent [19]
Eilers et al.

[11] Patent Number: 5,817,279
[45] Date of Patent: Oct. 6, 1998

[54] APPARATUS FOR PROCESSING FLUIDS, IN PARTICULAR BLOOD

[75] Inventors: Rolf Eilers; Karl-Heinz Hildinger; Helmut Mückter, all of Aachen, Germany

[73] Assignee: MEDOS Medizintechnik GmbH, Stolberg, Germany

[21] Appl. No.: 720,142

[22] Filed: Sep. 25, 1996

[30]   Foreign Application Priority Data

Sep. 25, 1995 [DE]   Germany .................. 195 35 346.3

[51] Int. Cl.⁶ .................................................. A61M 1/14
[52] U.S. Cl. .................. 422/46; 422/45; 422/48
[58] Field of Search .................. 422/45, 46, 48

[56]         References Cited

U.S. PATENT DOCUMENTS

| | | | |
|---|---|---|---|
| 3,849,071 | 11/1974 | Kayser | 422/45 |
| 3,939,078 | 2/1976 | Servas et al. | 210/436 |
| 3,996,027 | 12/1976 | Schnell et al. | 95/261 |
| 4,141,835 | 2/1979 | Schäel et al. | 210/321.81 |
| 4,239,729 | 12/1980 | Hasegawa et al. | 422/48 |
| 4,376,095 | 3/1983 | Hasegawa | 422/46 |
| 4,424,190 | 1/1984 | Mather, III et al. | 422/46 |
| 4,440,723 | 4/1984 | Gordon | 348/788 |
| 4,451,562 | 5/1984 | Elgas et al. | 435/2 |
| 4,876,066 | 10/1989 | Bringham et al. | 422/46 |
| 5,270,004 | 12/1993 | Cosentino et al. | 422/46 |

FOREIGN PATENT DOCUMENTS

| | | |
|---|---|---|
| 0 046 583 | 8/1981 | European Pat. Off. . |
| 0 257 279 B1 | 7/1987 | European Pat. Off. . |

*Primary Examiner*—Robert J. Warden
*Assistant Examiner*—Alex Noguerola
*Attorney, Agent, or Firm*—Henry M. Feiereisen

[57]         ABSTRACT

Apparatus for processing fluids, in particular blood, includes a housing having an fluid inlet port and a fluid outlet port, with the housing being formed by an outer tube, an intermediate tube set within the outer tube for forming a first chamber therebetween, and an inner tube set within the intermediate for forming a second chamber therebetween. Disposed within the chambers are a plurality of hollow fiber membranes for suitably conducting heat exchange fluid and gas. The first and second chambers are so interconnected to one another and the inlet port and outlet ports are so disposed as to effect a fluid flow path through the chambers in longitudinal direction of the tubes.

12 Claims, 2 Drawing Sheets

APPARATUS FOR PROCESSING FLUIDS, IN PARTICULAR BLOOD

BACKGROUND OF THE INVENTION

The present invention refers to an apparatus for processing fluids, especially blood, and in particular refers to a fluid processing unit of a type having a housing exhibiting a fluid inlet port and a fluid outlet port, with the housing being formed by tubes nested within each other to define several chambers in which hollow chamber membranes are received.

There are known a wide variety of extracorporeal blood oxygenation systems for oxygenating and heating a patient's blood during cardiovascular surgery or situations in which the heart and lungs do not properly function. Conventional blood oxygenators typically operate with hollow fibers that bring blood into contact with oxygen and are membranes usually made of gas-permeable material such as silicone or hydrophobic polymeric material such as polyolefins. These types of hollow fiber membranes are well known in the art and routinely used in membrane oxygenation systems of this type.

A blood oxygenator and heat exchanger device of this type is known e.g. from U.S. Pat. No. 5,270,004, issued on Dec. 14, 1993, which includes a closed housing receiving blood through a blood inlet port positioned centrally at the housing bottom. The blood flows through holes in a porous tubular wall in radial direction into an annular chamber which surrounds the tubular wall and accommodates a hollow fiber membrane to conduct a heat exchange fluid. Subsequently, the blood flows through openings in a second tube into a further annular chamber which contains hollow fiber membranes for conducting a gas. This chamber is surrounded by a third liquid-permeable annular wall through which blood flows radially into an annular collecting channel and from there to the blood outlet port.

This integrated blood heater-oxygenator assembly exhibits a compact structure and is suitable to accomplish a sufficient heat exchange and oxygenation of blood. However, this assembly has the drawback that the main blood flow direction proceeds diagonally from the central inlet port at the bottom to the outlet port in the peripheral area at the top of the assembly, thereby creating dead zones in the upper central areas and in the lower, peripheral area. Thus, different flow rates are experienced which decrease from a maximum flow rate in the area of the described diagonal to the dead zones. Moreover, manufacturing tolerances easily create breakages as a result of channel formation. These different flow rates lead locally to varying material exchange and heat exchange between the hollow chamber membranes and blood and thus to a reduced heat exchange action.

SUMMARY OF THE INVENTION

It is an object of the present invention to provide an improved apparatus for processing blood, obviating the afore-stated drawbacks.

In particular, it is an object of the present invention to provide an improved fluid processing apparatus which effects a substantially even fluid flow.

These objects and others which will become apparent hereinafter are attained in accordance with the present invention by providing a housing including a fluid inlet port and a fluid outlet port and exhibiting various chambers as formed by tubes nested within each other, with the chambers being so fluidly interconnected and the fluid inlet port and the fluid outlet port being so positioned as to effect a fluid stream within the chambers in longitudinal direction of the tubes.

While conventionally, the fluid flow is effected radially through the tubes, the fluid processing unit according to the present invention forces an axial flow direction through the chambers. This is attained by disposing the inlet into the chambers and the outlet from the chambers solely at their opposing axial ends. Thus, the entire fluid flow is forced to flow in longitudinal direction through the individual chambers before exiting the processing unit.

Persons skilled in the art will understand that the fluid processing unit according to the present invention is applicable as blood oxygenator of the inside perfusion type in which blood is passed through the interior of the hollow chamber membranes while oxygen flows outside of the hollow chamber membranes, or vice versa as in the outside perfusion type in which blood flows outside the hollow chamber membranes.

In order to provide a particular compact construction, the fluid processing unit has one tube which forms the outer wall surface of an inner chamber and at a same time the inner wall surface of an outer chamber. In this manner, the individual chambers are in immediate adjacent disposition so that material consumption is reduced and the overall dimensions are smaller. Moreover, the compact structure of the fluid processing unit effects a shortening of the connecting channels between the individual chambers.

A simplified structure and a shortening of the connecting channels is also attained by forming the chambers of substantially equal length. Preferably, also the hollow chamber membranes received within the chambers are of substantially equal length. Not only does this simplify the overall structure of the assembly but also accomplishes a cost-efficient production because potting and cutting of the hollow chamber membranes disposed within the chambers can be effected in a single operation.

The compact structure of the fluid processing unit according to the present invention is not only advantageous as far as the production is concerned but also results in a reduction of the priming volume, i. e. the air volume that has to be displaced during initial charging of the processing unit with fluid.

Preferably, the tubes are of slight conical configuration to effect a more cost-efficient potting process. Moreover, as frictional forces are reduced during assembly of the single components of the processing unit, the fibers are subject to less mechanical stress during assembly.

Shear stress can be minimized in the inlet area of the housing by incorporating in the inlet area a cyclone which in addition has the advantage of removing air bubbles from the blood stream prevalent in the inlet zone. Preferably, the cyclone is at least partially received within the center tube in order to create a space-saving incorporation of the cyclone within the processing unit and to effect short flow paths for the blood stream as well as a compact structure of the processing unit.

Advantageously, the fluid outlet of the housing is formed as ring channel which exhibits a cross section that increases in flow direction. As a result of such a ring channel, blood can be discharged at minimum priming volume in a careful manner from the chamber being passed last.

The individual chambers may receive various types of hollow chamber membranes. It is even possible to provide different types of hollow chamber membranes within a single chamber. Through suitable configuration of housing fittings, the chambers may also be used for conducting different fluids. The hollow chamber membranes may be formed of membrane plates, or preferably in the form of hollow fibers.

In accordance with a simple embodiment of a fluid processing unit according to the present invention, a first chamber accommodates hollow chamber membranes for conducting a heat exchange fluid to heat blood passing through the chamber passes in longitudinal direction along the outside of the membranes, and a second chamber accommodates hollow chamber membranes for conducting a gas to oxygenate blood that enters the second chamber after passing through the first chamber and is directed through the second chamber along the outside of the membranes. Advantageously, blood is first heated and subsequently oxygenated to execute oxygenation at uniform temperature conditions. As the gas solubility in blood and other liquids depends on the temperature, it is important to oxygenate blood at the temperature at which the blood enters the body. When heating blood after oxygenation, there is a risk to exceed the degree of saturation and to cause embolism in the body through free air bubbles.

In general, the oxygenator requires a greater heat exchange surface between membrane and blood than the heat exchanger so that it is advantageous to position the oxygenator radially outside of the heat exchanger. A rapid oxygenation of blood flowing through the processing unit is effected by arranging porous hollow fiber membranes within one chamber. Depending on the application of the processing unit, it is however also possible to utilize hollow fiber membranes of different membrane materials, and it is immaterial whether the blood oxygenator-heater assembly is operated as inside perfusion unit or outside perfusion unit. It is also conceivable to pass the fluids through chambers in parallel relationship or in successive disposition in order to best suit the field of application of the processing unit.

Advantageously, the hollow fiber membranes in one chamber conduct a heat exchange fluid and the hollow fiber membranes in the other chamber conduct a gas while blood flows through the chambers outside of the membranes. The conduction of blood through the chambers results in a minimizing of the priming volume and a careful blood transport. As the hollow chamber membranes can be suited to conduct different fluids, a defined conditioning of the fluid that passes through the processing unit is attained.

BRIEF DESCRIPTION OF THE DRAWING

The above and other objects, features and advantages of the present invention will now be described in more detail with reference to the accompanying drawing in which.

DETAILED DESCRIPTION OF A PREFERRED EMBODIMENT

Figure 1:
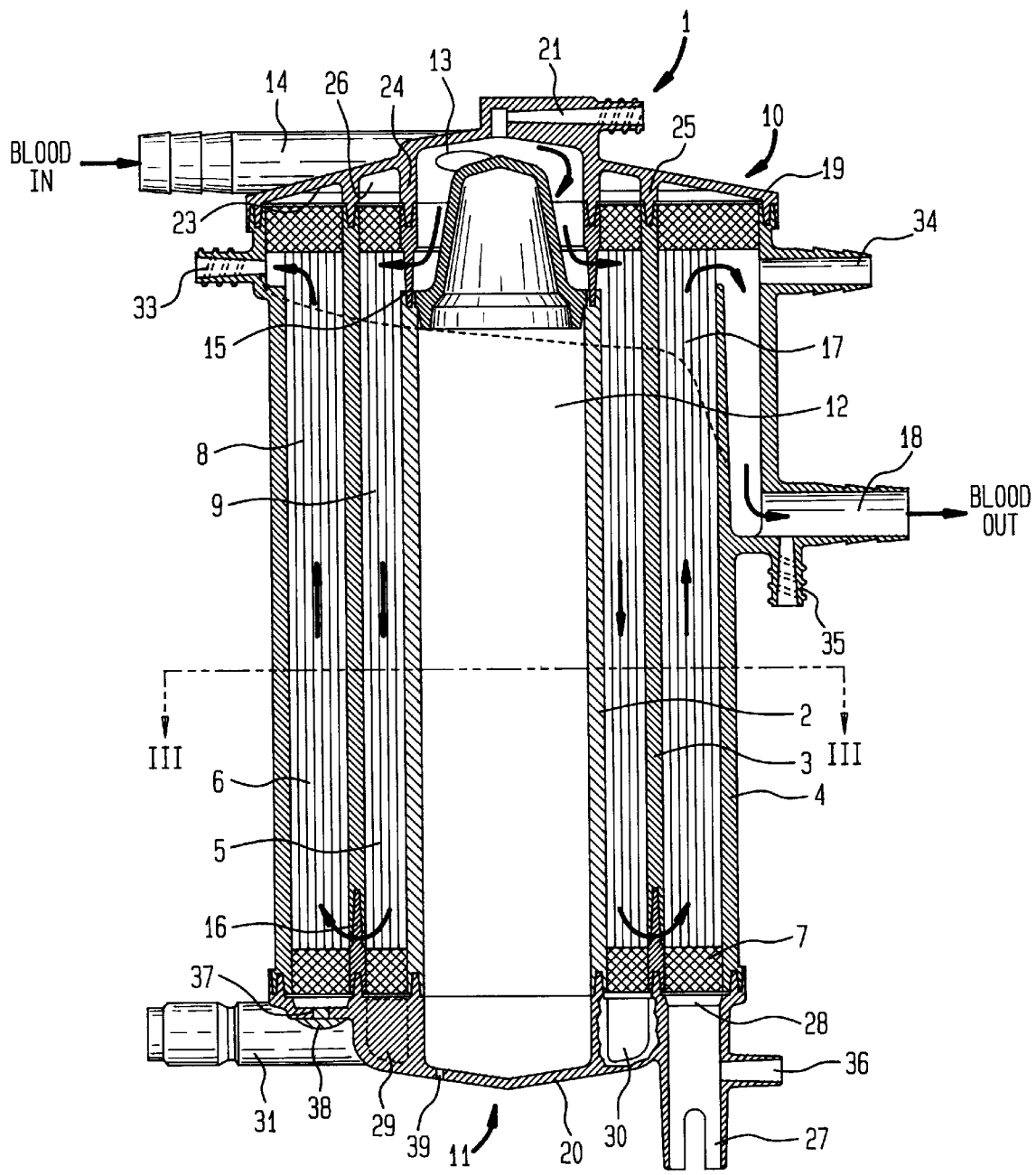
FIG. 1 shows an axial sectional view of one embodiment of a fluid processing unit according to the present invention.

Throughout all the Figures, the same or corresponding elements are always indicated by the same reference numerals.

Turning now to the drawing, and in particular to FIG. 1, there is shown an axial sectional view of one embodiment of a fluid processing unit according to the present invention, generally designated by reference numeral 1, for heating and oxygenating a fluid, e.g. blood. Such a processing unit is called "blood oxygenator and heat exchanger" and includes a generally cylindrical closed housing which is essentially formed by three coaxial tubes nested within each other, with an inner central tube 2 set within an intermediate tube 3 to form an inner chamber 5 therebetween, and an outer tube 4 which surrounds the intermediate tube 3 to define an outer chamber 6 therebetween. The ends of the inner chamber 5 and the outer chamber 6 are closed by a potting material 7. Hollow fiber membranes 8, 9 are disposed within the chambers 5, 6 and held together by the potting material 7 in such a manner that the openings of the hollow fiber membranes are positioned outside of the chambers 5, 6 to isolate the open ends of the hollow fiber membranes 8, 9 from the flow path of the fluid being treated.

The tubes 2, 3, 4 are of slight conical configuration so that their cross section at the top 10 is greater than the cross section at the bottom side 11.

The inner tube 2 surrounds a hollow space 12. Mounted to the tube 2 at the upper area of the hollow space 12 is a cyclone 13 which has an inlet port 14 for incoming fluid being treated, e.g. blood. The exit opening 15 of the cyclone 13 is formed at the upper end of the inner tube 2 for allowing blood to flow from the inlet port 14 through the cyclone 13 into the inner chamber 5. In the lower area of the chambers 5, 6, the intermediate tube 3 is provided with openings 16 for interconnecting the inner chamber 5 with the outer chamber 6 so that blood entering the inner chamber 5 through cyclone outlet 15 streams downwardly in longitudinal direction towards the openings 16 where the blood flow is deflected into the outer chamber 6. The outer tube 4 expands radially at the upper end in a peripheral zone 17 in order to connect with a blood outlet port 18 in a spiral-type manner.

Figure 2:
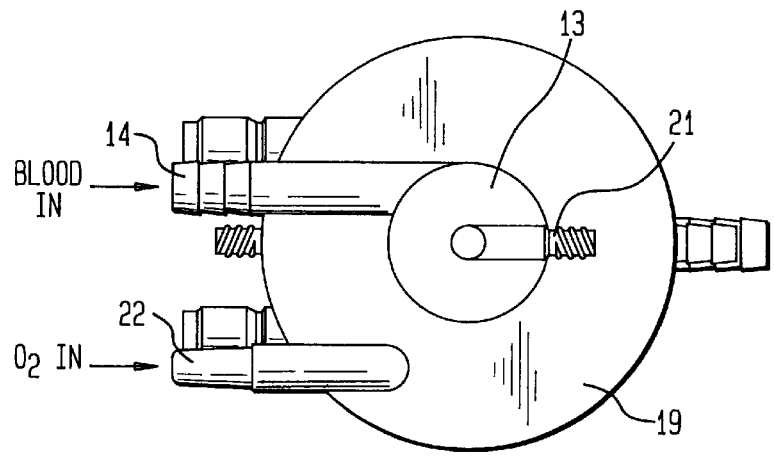
FIG. 2 is a top view of the fluid processing unit of FIG. 1.

The top 10 of the housing is closed by an upper lid 19 while the bottom 11 of the housing is closed by a lower lid 20. As shown in FIG. 2, the blood inlet port 14 is positioned in the upper lid 19 in such a manner that the incoming blood flows towards the cyclone 13 in a tangential direction. Positioned at the apex of the cyclone 13 is a vent 21 by which air accumulating in the cyclone 13 is removed. As further shown in FIG. 2, the upper lid 19 is additionally provided with a gas inlet port 22 which leads into an upper gas space 23 that is bounded by the lid 19 and the potting material 7. Axial webs 24, 25 extend downwardly from the lid 19 towards the tubes 2, 3, 4 and define an upper liquid space 26 for deflecting water conducted in the hollow fiber membranes 9 of the inner chamber 5.

Figure 3:
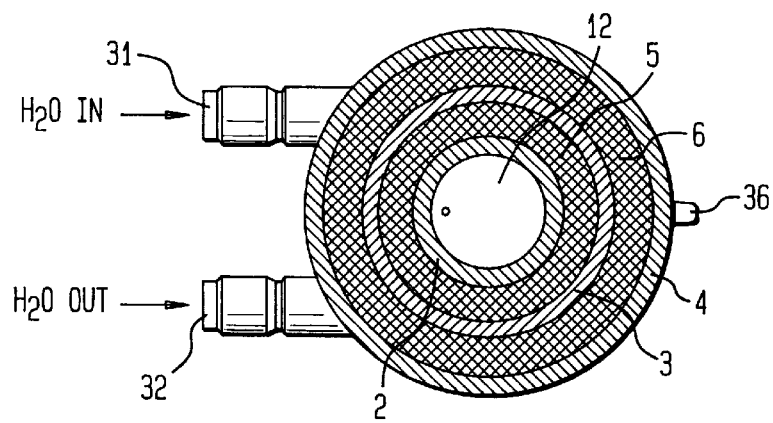
FIG. 3 is a sectional view of the fluid processing unit, taken along the line III—III in FIG. 1.

The bottom lid 20 is formed with a gas outlet port 27 in form of an axial pipe which leads to a lower gas space 28 formed between the lid 20 and the potting material 7 beneath the outer chamber 6. As shown in FIG. 1, the lid 20 is further formed within an ring channel 30 which is divided by two plates 29 into two sections. FIG. 1 shows on the left hand side the plate 29 in broken lines while on the right hand side, the plate is broken away to illustrate the ring channel 30. One section of the ring channel 30 is in communication with a water inlet port 31 while the other side of the ring channel 30 is fluidly connected to a water outlet port 32, as shown in FIG. 3.

Figure 4:
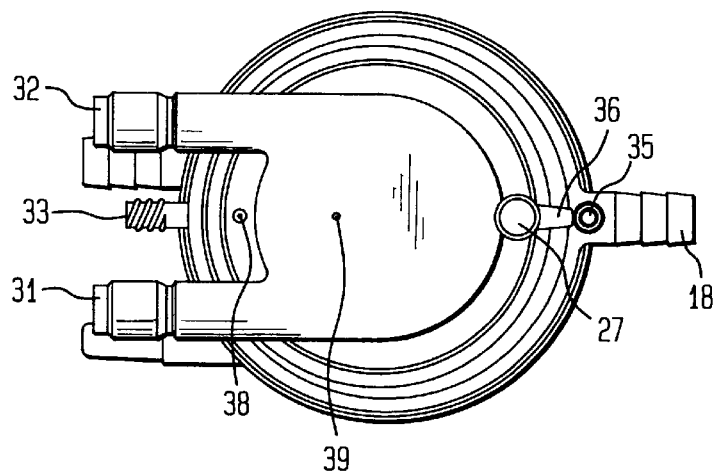
FIG. 4 is a bottom view of the fluid processing unit.

As shown in particular in FIG. 4, the housing of the processing unit 1 is formed on the side opposite to the blood outlet port 18 with a fitting 33 for receiving a temperature probe. The fitting 33 may also be used as a vent opening. The housing is further provided on the upper end of the outer chamber 6 directly above the blood outlet port 18 with a further blood outlet port 34 for use with a recirculation conduit which forms a bypass through which a blood volume flow can be conducted into a reservoir (not shown).

On the underside of the blood outlet port 18 is a fitting 35 for allowing withdrawal of blood samples or introduction of other measuring implements. A horizontal fitting 36 branches off from the gas outlet port 27 for allowing measurement of the pressure or temperature of gas exiting through outlet port 27. In opposition to the gas outlet port 27, the gas space 28 is formed with a pressure opening 37 which is closed by a plug 38 and opens at excessive pressure on the gas side. The lower lid 20 is further formed with a compensation port 39 that connects the hollow space 12 with the outside for pressure compensation.

At operation of the fluid processing unit 1, warm water is introduced through the inlet port 31 to one side of the ring channel 30 and is directed to the hollow fiber membranes 9 arranged within the inner chamber 5. Water rises within the hollow fiber membranes 9 until reaching the liquid space 26 in the upper lid 19. Within the liquid space 26, the water is distributed and flows back through the remaining hollow fiber membranes 9 within the inner chamber 5 downwards towards the other side of the ring channel 30 for exiting through the water outlet port 32. Gas is introduced through the inlet port 22 and flows into the upper gas space 23 in the upper lid 19 and through the hollow fiber membranes 8, disposed in the outer chamber 6, downwards towards the lower gas space 28 in the lid 20. Subsequently, the gas exits through the outlet port 27.

The fluid being treated, e.g. blood, is introduced into the processing unit 1 through inlet port 14 to flow into the cyclone 13 where the blood is conducted along a spiral-shaped path downwards until reaching the outlet 15 for entry into the inner chamber 5. The blood stream flows in longitudinal direction outside the hollow fiber membranes 9 while being heated by water conducted in the hollow fiber membranes 9. After reaching the lower end of the chamber 5, the blood stream enters the openings 16 and is deflected into the outer chamber 6 to flow upwards in longitudinal direction outside the hollow fiber membranes 8 through which gas is conducted. Thus, the blood stream is enriched with oxygen. After reaching the upper end of the outer chamber 6, the blood stream flows along a circular path towards the blood outlet port 18 for discharge from the processing unit 1.

Both, the inner chamber 5 and the outer chamber 6 are formed at their upper ends with openings for discharge of air that rises within the chambers 5, 6. Air in the inner chamber 5 exits through the outlet 15 into the cyclone 13 and from there through the vent 21 to the outside while air in the outer chamber 6 is discharged through the fitting 33 or the additional blood outlet port 34. Thus, the processing unit 1 is vented in an optimum manner during operation and during the initial charging operation.

While the invention has been illustrated and described as embodied in a apparatus for processing fluids, in particular blood, it is not intended to be limited to the details shown since various modifications and structural changes may be made without departing in any way from the spirit of the present invention.

What is claimed as new and desired to be protected by Letters Patent is set forth in the appended claims:

1. Apparatus for processing blood, comprising:
    a housing having a fluid inlet port and a fluid outlet port, said housing being formed by an outer tube, an intermediate tube set within the outer tube for forming a first chamber therebetween, and an inner tube set within the intermediate tube for forming a second chamber therebetween; and
    a plurality of hollow fiber membranes provided in the first and second chambers;
    wherein said outer, intermediate and inner tubes are formed by walls so configured that said first and second chambers are fluidly connected to one another as to effect a fluid flow path through the first and second chambers in longitudinal direction of the tubes between said inlet and outlet ports of said housing.

2. The apparatus of claim 1 wherein the intermediate tube forms an outer wall surface of the second chamber and an inner wall surface of the first chamber.

3. The apparatus of claim 1 wherein the first and second chambers are of substantially equal length.

4. The apparatus of claim 1 wherein the hollow fiber membranes are of substantially equal length.

5. The apparatus of claim 1 wherein the tubes are of conical configuration.

6. The apparatus of claim 1, and further comprising a cyclone received in the inlet port.

7. The apparatus of claim 6 wherein the cyclone is disposed at least partially in the inner tube.

8. The apparatus of claim 1 wherein the outlet port is formed as ring channel exhibiting a cross section increasing in flow direction.

9. The apparatus of claim 1 wherein the hollow fiber membranes within the first chamber are of porous configuration.

10. The apparatus of claim 1 wherein the hollow fiber membranes in one of the first and second chambers conduct a heat-exchange fluid and the hollow fiber membranes in the other one of the first and second chambers conduct a gas while fluid flows through the first and second chambers outside of the hollow fiber membranes.

11. A blood oxygenator and host exchanger unit, comprising:
    a housing having a blood inlet port and a blood outlet port, and a plurality of chambers formed by tubes nested within each other for providing a passageway for blood to flow from the blood inlet port to the blood outlet port, said tubes being formed by walls so configured that said chambers are fluidly interconnected as to provide a blood flow path through the chambers in longitudinal direction between said inlet and outlet ports of said housing; and
    a plurality of hollow fiber membranes provided in the chambers for conducting a heat-exchange fluid in one of the chambers and conducting a gas in another one of the chambers.

12. The blood oxygenator and heat exchanger of claim 11 wherein each of the chambers defines a proximal end and a distal end and is configured in such a manner that each of the chambers has an entrance and an exit at the proximal and distal ends.

* * * * *